United States Patent
Zal (10) Patent No.: US 10,119,110 B2
(45) Date of Patent: Nov. 6, 2018

(54) BIOREACTOR USING OXYGEN-CARRYING MOLECULES

(75) Inventor: Frank Zal, Morlaix (FR)

(73) Assignee: HEMARINA, Morlaix (FR)

( * ) Notice: Subject to any disclaimer, the term of this patent is extended or adjusted under 35 U.S.C. 154(b) by 207 days.

(21) Appl. No.: 13/265,642

(22) PCT Filed: Apr. 21, 2010

(86) PCT No.: PCT/EP2010/055307
§ 371 (c)(1),
(2), (4) Date: Oct. 21, 2011

(87) PCT Pub. No.: WO2010/122080
PCT Pub. Date: Oct. 28, 2010

(65) Prior Publication Data
US 2012/0040453 A1  Feb. 16, 2012

Related U.S. Application Data (60) Provisional application No. 61/171,988, filed on Apr. 23, 2009.

(30) Foreign Application Priority Data

Jul. 2, 2009  (EP) .................. 09305640

(51) Int. Cl.
*C12M 3/06* (2006.01)
*C12M 1/04* (2006.01)
*C12M 1/00* (2006.01)

(52) U.S. Cl.
CPC ............ *C12M 23/24* (2013.01); *C12M 23/34* (2013.01); *C12M 29/04* (2013.01)

(58) Field of Classification Search
CPC ....... C12M 23/24; C12M 23/34; C12M 29/04
(Continued)

(56) References Cited

U.S. PATENT DOCUMENTS 1,494,950 A * 5/1924 Clark ...................... B65D 75/32
                                                      206/484
3,997,396 A * 12/1976 Delente ................. C12M 25/10
                                                      435/400
(Continued)

FOREIGN PATENT DOCUMENTS

GB    2075547 A  * 11/1981  ............... C02F 3/06
SU    1400575 A1 *  6/1988
WO    9527041 A   10/1995

OTHER PUBLICATIONS

Wuhrer et al. A novel Gal(beta1-4)Gal(beta1-4)Fuc(alpha1-6)-core modification attached to the proximal N-acetylglucosamine of keyhole limpet haemocyanin (KLH) N-glycans. Biochem. J. 2004;378:625-632.*

(Continued)

*Primary Examiner* — William H. Beisner
(74) *Attorney, Agent, or Firm* — Young & Thompson (57) ABSTRACT

The present invention relates to devices and bioreactors capable of delivering oxygen to a cell culture using oxygen-carrying molecules. The bioreactor comprises at least two chambers separated by an oxygen-permeable membrane. The oxygen-carrying molecules are chosen from extracellular hemoglobin isolated from worm belonging to Arenicoliolae family or Nereidiolae family.

7 Claims, 8 Drawing Sheets

(58) Field of Classification Search
USPC .................................................... 435/297.2
See application file for complete search history.

(56) References Cited

U.S. PATENT DOCUMENTS

| | | | | |
|---|---|---|---|---|
| 4,559,053 A | * | 12/1985 | Porges | A61J 1/10 |
| | | | | 206/463 |
| 4,661,455 A | * | 4/1987 | Hubbard | C12M 23/14 |
| | | | | 435/297.1 |
| 5,223,428 A | | 6/1993 | Rose | |
| 5,374,243 A | * | 12/1994 | Whalen | A61M 37/00 |
| | | | | 128/898 |
| 2003/0181358 A1 | * | 9/2003 | Zal et al. | 514/6 |
| 2006/0199260 A1 | | 9/2006 | Zhang et al. | |

OTHER PUBLICATIONS

English language machine translation of SU 1400575 A1 (Jun. 1988), 6 pages.*
Garlick et al. : "Structure and Oxygen Equilibrium of Hemoglobin and Myoglobin From the Pacific Lugworm *Abarenicola pacifica*", Comp. Biochem. Physiol., vol. 57B, 1977, pp. 177-184, XP002596822.
International Search Report, dated Aug. 26, 2010, in Application No. PCT/EP2010/055307.

* cited by examiner

BIOREACTOR USING OXYGEN-CARRYING MOLECULES

FIELD OF THE INVENTION

The invention relates to a new bioreactor or device capable of delivering oxygen to cell culture using an oxygen carrier which functions in a simple gradient of partial pressure of oxygen.

BACKGROUND OF THE INVENTION

There is increasing interest in the production of important biologicals by animal cell culture using more efficient technology to meet demands in quantity, purity and safety for these products, preferably at reduced unit cost. Scale-up of the traditional batch culture has in practice several technical and economic limitations resulting from the low product titer and poor volume productivity. An alternative method is intensification of the reaction process by recycling or retaining cells in the bioreactor. In such cultures, cells can be maintained at high density through a retention system that can allow cells to be perfused with fresh medium while withdrawing spent medium at the same time. In this context of high density culture, oxygen is not only essential for cell growth but also for the maintenance of cell viability and need to be delivered gradually in function of cell demand. Even within the range of oxygen concentrations sufficient for cell survival, the concentration of oxygen has a profound influence on cell signaling, growth factor production, growth and differentiation (Muschler et al. 2004). Excess levels of dissolved oxygen may enhance the formation of superoxide radicals, peroxides and hydroxyl radicals, which can damage the DNA and cell membranes, reduce cell viability, induce cell death and create the condition of "oxidant stress" (Ellis 1991; Cacciuttolo et al. 1992). The inhibition of cell growth in such conditions may be due to the formation of peroxides and free radicals, which "down-regulate" cell proliferation, reduce cell viability and create the condition of "oxidant stress" (Ellis 1991). These oxidising agents are responsible for damaging cellular materials such as DNA, carbohydrates and proteins. An elevated dissolved oxygen level has also been shown to prolong cell-cycle duration by inhibiting the initiation of DNA synthesis (Barlin et al. 1979). More recently, Cacciuttolo et al. (1992) provided evidence that dissolved oxygen concentrations higher than 100% caused increased DNA strand breaks as well as affecting metabolic functions such as glucose consumption rate, lactate production rate and cell growth. Typical demands for oxygen by animal cells during batch culture are in the range $2\times10^{-16}$-$2\times10^{-15}$ mol $O_2$ cell$^{-1}$ min$^{-1}$. It is not difficult to cope with this oxygen requirement in low-cell-density batch or continuous cultures, at least for small scales of operation, but meeting the oxygen demand in high-cell-density perfusion cultures is a serious problem. In addition, enhancing bacteria and cell growth represents an economic challenge for bio-industry.

Different approaches have been developed to supply oxygen in cell cultures. In general, the growth and/or culture of animal cells, especially mammalian cells requires a constant supply of oxygen and effective removal of gaseous metabolic by-products, mainly carbon dioxide. The requisite gas exchange can be accomplished in a number of ways, including agitation of the reaction vessel and bubbling of oxygen-containing gases through the culture. In order for agitation to be effective, very low volumes of culture medium must be used since the effectiveness of this method depends on exposure of all of the cells in the culture to the surface. Bubbling of gases obviates this problem to some extent, but superimposes another wherein sufficient bubbling to be effective creates shear forces believed to be harmful to the relatively delicate animal cell membranes.

Another approach to supply oxygen in a fermentation vessel for animal cells consists in using a tube or hose of a synthetic polymer, such as silicone rubber, laminated silicone rubber products, or a polytetrafluoroethylene (Teflon®), to provide oxygen through diffusion (U.S. Pat. No. 4,649,114). This tube is required to be non adherent with regard to the cells, thick enough to provide mechanical strength, and thin enough to permit oxygen to pass through readily.

Another examples of devices allowing the supply of oxygen through a membrane are the hollow fiber systems (FiberCell®, Cellco®, Technomouse® from Integra Biosciences), which rely on the supply of oxygen along with culture medium through a closely spaced series of hollow fibers interspersed among the suspended cell culture. One drawback of this hollow fiber system is that the cells have to be in close proximity to the fibers to be supplied in oxygen.

The present invention aims to provide a new generation of bioreactor capable of delivering oxygen to cell culture using oxygen carrying molecules. In this new generation of bioreactor, oxygen can be delivered to the cells progressively according to the biomass growth avoiding stress and cell damages linked to oxygen excess.

Particularly, the present invention aims to provide a new generation of bioreactor capable of delivering oxygen to cell culture by means of oxygen carrying molecules, without using any cofactor.

SUMMARY OF THE INVENTION

An object of the present invention is an oxygen-carrying molecules receptacle, comprising:
  a chamber at least partially defined by an oxygen-permeable membrane and
  a plurality of oxygen-carrying molecules contained within said chamber.

In one embodiment, said oxygen-carrying molecule receptacle comprises a chamber entirely defined by an oxygen-permeable membrane.

In another embodiment, said oxygen-carrying molecule receptacle comprises a chamber partially defined by an oxygen-permeable membrane and partially defined by at least one substantially rigid panel.

Another object of the invention is a bioreactor comprising:
  at least one first chamber adapted to receive cells in a culture medium,
  at least a second chamber further comprising at least one oxygen inlet.

Another object of the invention is a bioreactor comprising:
  at least one first chamber adapted to receive cells in a culture media,
  at least a second chamber comprising at least one oxygen inlet and adapted to receive oxygen-carrying molecules,
  at least one oxygen-permeable membrane adapted to allow oxygen diffusion between the oxygen carrying molecules of said first chamber and said second chamber,
  wherein the second chamber contains oxygen-carrying molecules.

In one embodiment, the second chamber of said bioreactor comprises a guide system adapted to guide the oxygen received from the oxygen inlet of the second chamber to the oxygen-permeable membrane.

Another object of the invention is a bioreactor comprising:
- at least one first chamber adapted to receive cells in a culture medium,
- at least a second chamber comprising at least one oxygen inlet and adapted to receive oxygen carrying molecules,
- at least one oxygen-permeable membrane adapted to allow oxygen diffusion between the oxygen carrying molecules of said first chamber and the culture media of the second chamber, wherein the second chamber comprises a guide system adapted to guide the oxygen received from the oxygen inlet of the second chamber to the permeable membrane.

In one embodiment, the second chamber of said bioreactor contains oxygen-carrying molecules.

In one embodiment of the invention, the oxygen carrying molecules contained in the above described receptacles or in the second chamber of the above described bioreactors are selected from the group consisting of: hemoglobin-based oxygen carriers, perfluorocarbons and extracellular hemoglobins isolated from annelids.

In another embodiment, said oxygen carrying molecules are extracellular hemoglobins isolated from worms belonging to Arenicolidae family or Nereididae family.

In another embodiment, said oxygen carrying molecules are in an aqueous solution.

In another embodiment, said oxygen carrying molecules are selected from the group consisting of: hemoglobin-based oxygen carriers and extracellular haemoglobins isolated from annelids and are in a lyophilized or thawed form.

In one embodiment, the guide system of the above described bioreactors comprises a oxygen-permeable tube and a circulating device.

In one embodiment, the oxygen-permeable tube of said guide system is winding.

In another embodiment, the above described bioreactors further comprise at least one inflow port connected to the first chamber to allow fresh culture medium to be continuously supplied to the first chamber and at least one outflow port connected to the first chamber to allow culture medium to be continuously removed from the first chamber.

Another object of the invention is a kit comprising:
- one of the bioreactors described above,
- a container comprising oxygen carrying molecules as described above.

Another object of the invention is a method of oxygenating a cell culture, comprising:
contacting a cell culture with oxygen-carrying molecules through a oxygen-permeable membrane,
such that the oxygen-carrying molecules discharge oxygen to the cell via the oxygen-permeable membrane.

Various features and advantages of this invention will become apparent to those skilled in the art from the following detailed description of various embodiments, the drawings of which will help illustrate these embodiments.

DETAILED DESCRIPTION OF THE INVENTION

In the following description, the same references denote identical or similar elements, and are in no way limiting.

The present invention relates to a method of oxygenating a cell culture, comprising:
contacting a cell culture with oxygen-carrying molecules through a oxygen-permeable membrane, such that the oxygen-carrying molecules discharge oxygen to the cell via the oxygen-permeable membrane.

As used herein, the cell culture refers to any type of cells in any type of medium.

It is to be noted that it is not necessary for the oxygen-carrying molecules to be in direct physical contact with the oxygen-permeable membrane; as such, as used herein, the term 'adjacent' refers to a position next to but not necessarily contacting the oxygen-permeable membrane. Advantageously, however, the oxygen-carrying molecules are as close as possible to, preferably in direct physical contact with, the oxygen-permeable membrane.

Indeed, the oxygen-carrying molecules function in a simple gradient of partial pressure of oxygen. Thus, when $pO_2$ of the cell culture is inferior to the $p_{50}$ of the oxygen-carrying molecules, oxygen is released from the molecules. Therefore, the cell culture is oxygenated via the oxygen-carrying molecules and this oxygenation respects the cell culture needs as its follows the $pO_2$ that is function of cell growth.

Figure 10:
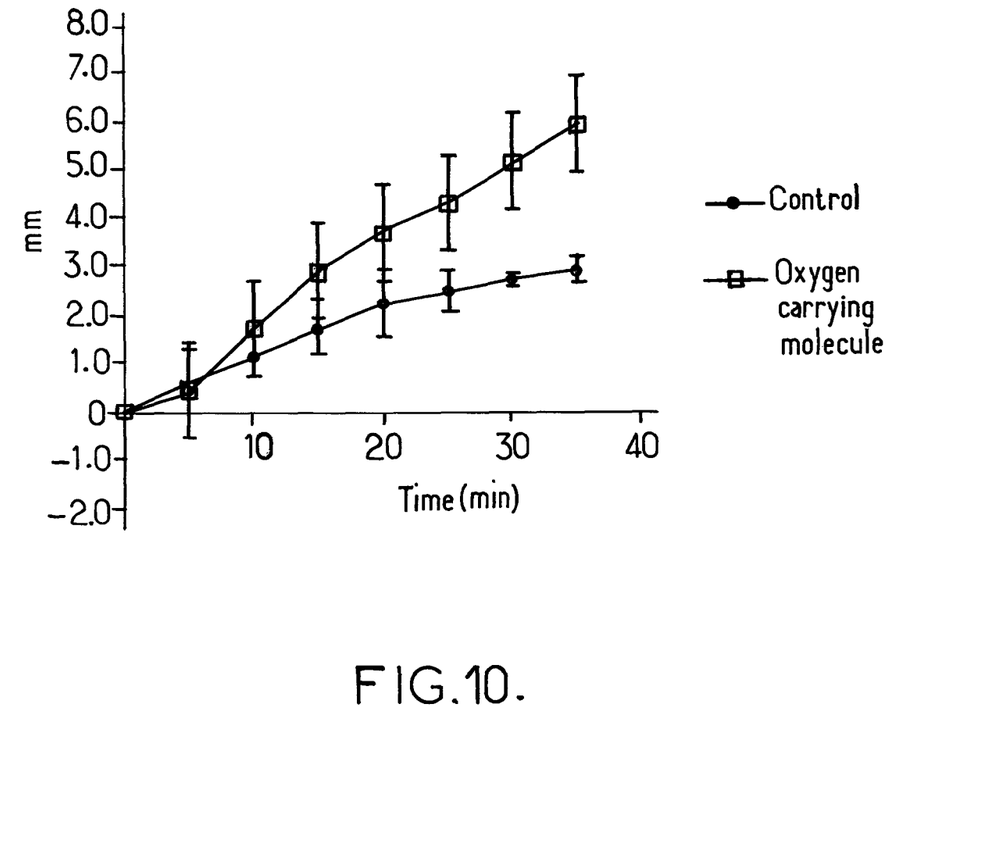
FIG. 10: comparison of oxygen diffusion across an oxygen-permeable membrane according to the present invention.

As shown in FIG. 10, oxygen diffusion across an oxygen-permeable membrane is considerably increased when oxygen-carrying molecules are used according to the present invention, compared to simple oxygen diffusion directly through the cell culture.

According to the invention, the oxygen-permeable membrane is a membrane through which oxygen is able to diffuse. Examples of oxygen-permeable membranes include, but are not limited to, membranes fabricated with fluoropolymer, polytetrafluoroethylene (TEFLON®), silicone, poly (methyl methacrylate) (PMMA) or polydimethylsiloxane (PDMS).

In general, said oxygen-permeable membrane may provide a 0.2 μm vent barrier.

In certain embodiment of the invention, the permeability (i.e. product of diffusivity or solubility) of the membrane to oxygen is approximately equal to that of PDMS, i.e. 800 barrer (1 Barrer=$10^{-11}$ ($cm^3 O_2$) cm $cm^{-2}$ $s^{-1}$ $mmHg^{-1}$). In certain other embodiments of the invention the permeability of the membrane to oxygen is greater than 800 Barrer. In certain other embodiments of the invention the permeability of the membrane to oxygen is either between approximately 600 and 800 Barrer, between approximately 400 and 600 Barrer, between approximately 200 and 400 Barrer, or between approximately 80 and 200 Barrer.

In another embodiment, said oxygen-permeable membrane is optically transparent.

PDMS represents an attractive choice for the oxygen-permeable membrane fabrication for a number of reasons. PDMS is highly permeable to gas, which allows sufficient oxygen to diffuse into the medium while simultaneously allowing carbon dioxide and other gases to escape. PDMS is highly hydrophobic, which minimizes water loss to evaporation. It is biocompatible, can withstand autoclaving temperatures, and is transparent to visible light. Poly(methyl methacrylate) (PMMA) represents another attractive material for fabricating the oxygen-permeable membrane. This material offers greater mechanical stability while also providing excellent optical transparency in the visible region, which is important for systems that include an optical sensor. In general, other materials that provide a high degree of optical transparency can also be used. Typically such materials will transmit electromagnetic radiation without substantial scattering and/or absorption over thicknesses of interest herein. For example, preferred materials may attenuate incident electromagnetic radiation by 50% or less, 75% or less, 85% or less, 90% or less, 95% or less, or 99% or less, over a path length of 1 cm, 1 mm, 0.5 mm, 1 mm, etc. The transparency of a material can vary in a wavelength-dependent manner. Preferred materials have a high degree of transparency over wavelengths ranging between approximately 400 and 1100 nm, preferably between approximately 400 and 800 nm.

According to the invention, the oxygen-carrying molecules are isolated or engineered biological molecules that are capable of charging and discharging oxygen. Said oxygen-carrying molecules are selected from a group consisting of, but not limited to, for example: hemoglobin-based oxygen carriers, perfluorocarbons and extracellular haemoglobins isolated from annelids, preferably from marine annelids.

Haemoglobin-based oxygen carriers (HBOCs) and perfluorocarbons (PFCs) are two viable categories of oxygen therapeutics that currently exist. Haemoglobin taken directly from red blood cells cannot be used as an oxygen carrier. To avoid spontaneous breakdown of haemoglobin and the toxicity of haemoglobin extracted from red blood cells, haemoglobin-based oxygen carriers use purified human haemoglobin (Riess et al. Chem Rev 2001, 101:2797), animal (bovine) haemoglobin (Lok et al Nature 2001, 410:855) or recombinant haemoglobin (Looker et al Nature 1992, 356: 258) as raw materials. Each chain of purified haemoglobin is then covalently bridged with other globin chains or microencapsulated. Perfluorocarbons are liquid fluorinated hydrocarbon compounds capable of dissolve large amount of oxygen and then deliver this oxygen.

Examples of HBOCs include, but are not limited to, cross-linked haemoglobins such as Oxyfluor® from Hemagen, HemAssist® from Baxter; polymerized haemoglobins such as PolyHeme® from Northfield laboratories, Hemopure® from Biopure; or conjugated haemoglobins such as PHP® from Apex Bioscience, Hemospan® from Sangart.

Examples of PFCs include, but are not limited to, Oxygent® from Alliance or Oxycyte® from Synthetic blood.

In another embodiment, the extracellular heamoglobins isolated from marine annelids are isolated from worms belonging to Arenicolidae family or Nereididae family. These extracellular hemoglobins are very useful because they do not need any cofactor for delivering oxygen.

Preferably, said haemoglobin are isolated from *Arenicola marina* or from *Nereis virens*, also called *Nereis diversicola, Neanthes virens* or *Hediste diversicolor.*

In a first embodiment of the invention, the oxygen-carrying molecules are contained in a receptacle made entirely or in part of an oxygen-permeable membrane. In this embodiment, when the receptacle is contacted with a cell culture, the oxygen-carrying molecules can discharge oxygen trough the oxygen-permeable membrane to the cell culture according to the difference between the $pO_2$ of the cell culture and the $p_{50}$ of the oxygen-carrying molecules, so as to oxygenate the cell culture when needed.

For instance, the receptacle according to the first embodiment may be immersed in a volume of suitable cell culture, for example in a container or a chamber containing cell culture.

Figure 1A:
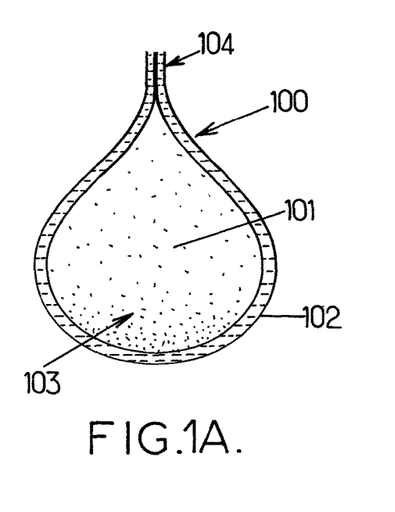
FIG. 1A is a transverse plan view of a receptacle according to a first embodiment of the invention.

FIG. 1A illustrates a receptacle 100, comprising:
 a chamber 101 defined entirely by an oxygen-permeable membrane 102, and
 a plurality of oxygen-carrying molecules 103 contained within the chamber 101.

The membrane 102 may for example be a flat sheet of oxygen-permeable membrane wrapped around the molecules 103, whereby its free ends are tied up to a sealed constriction point 104, for example by heat sealing, tie wrapping, or similar in such a way as to define a sealed volume representing the chamber 101.

The chamber 101 may for example be tea-packet shaped, enclose entirely the molecules 103. It is to be understood that tea-packet shaped comprises, for example, the shapes:
 substantially flat, parallel sided tea bag,
 a bulbous shaped tea bag,
 a pyramidal shaped tea bag,
 or similar.

Figure 1B:
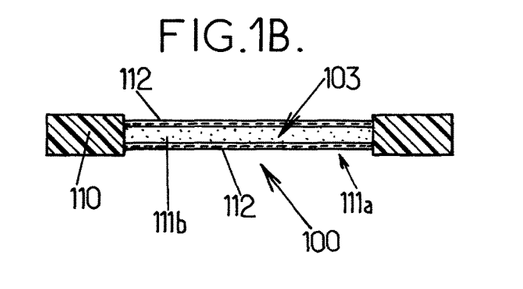
FIGS. 1B and 1C are, respectively, transverse vertical and top plan views of a variant of the receptacle of FIG. 1A.
Figure 1C:
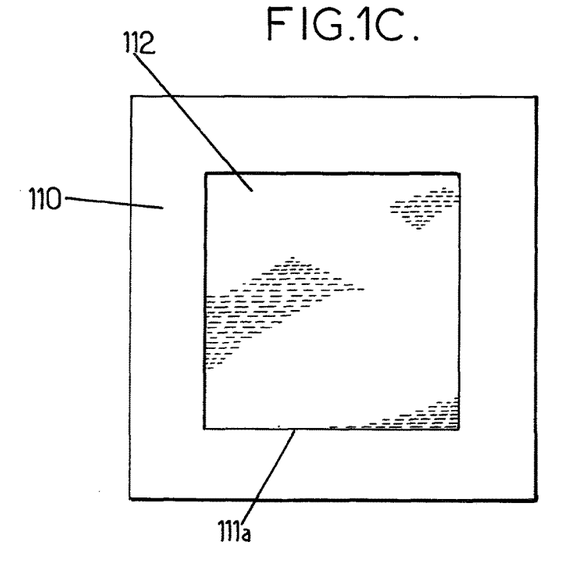

FIGS. 1B and 1C illustrate a variant of the receptacle 100 of FIG. 1a, wherein the receptacle takes the form of a semi-rigid cassette. In this variant, the receptacle 100 comprises:
 at least one substantially rigid panel 110 defining a cutout 111a within its central portion, the cutout defining a volume 111b adapted to receive a plurality of oxygen-carrying molecules 103, and
 two oxygen-permeable membranes 112 covering the cutout 111a, sitting preferably substantially flush with the respective upper and lower flat surfaces of the rigid panel 110.

The oxygen-permeable membrane 112 may be attached to the substantially rigid panel 110 using any technique known by the skilled person, and may for example be attached to the rigid panels 110 of the housing by fixing means, for example adhesion, crimping, thermosealing, etc.

The volume 111b is therefore closed and bound by the panel 110 on its lateral sides, and by the two membranes 103 on its upper and lower sides.

The volume 111b is filled with oxygen-carrying molecules 103.

According to this variant, the substantially rigid panel 110 is fabricated at least in part from a material which is not permeable to oxygen: for example, polymeric material such as polystyrene, plastics such as poly(carbonate), polypropylene, plexiglass, or copolymers of aromatics and polyolefins, which can be processed using standard methods such as free-form molding, micromolding, injection molding (e.g., reaction or thermoplastic injection molding, punching, etc.), hot embossing, CNC machining, laser direct write, microelectrodischarge machining, etc. Thermal bonding of thermoplastic materials is another useful technique that may be used.

In other variants, biocompatible materials (i.e., materials that will not significantly inhibit or adversely affect cell viability and proliferation and/or adversely affect other biological components such as metabolites produced by the cells) may be employed. Suitable materials include silicon, silicon dioxide (e.g., glass), ceramics, plastics such as poly(carbonate)s, acrylates, polypropylenes, polyethylenes, polyolefins, etc. In addition, nonbiocompatible materials (e.g., certain metals) may be employed provided they are coated with a biocompatible material.

The receptacle 100 as illustrated in FIGS. 1A to 1C may have any suitable size or geometric shape but one must be selected so that there may be sufficient oxygen diffusion across the oxygen-permeable membrane 102 to supply the required amounts of oxygen needed for cell metabolism. Those skilled in the art will be able to adapt these features, and the material of which the membrane is made, to the customary bio-technological requirements. Preferably, the size and shape of the receptacle 100 will be adapted to the bioreactor containing the cell culture with which the receptacle is going to be in contact.

In one embodiment of the invention, the receptacle as described above contains said oxygen-carrying molecules in an aqueous solution.

In another embodiment of the invention, when the oxygen-carrying molecules are selected in the group of HBOCs and haemoglobin isolated from marine annelids, said oxygen-carrying molecules may be in a lyophilized form.

In another embodiment, when the oxygen-carrying molecules are haemoglobins isolated from marine annelids, said oxygen-carrying molecules may be thawed.

In these last two embodiments, the oxygen-carrying molecules may be dissolved in any buffer suitable for cell culture, preferably a sterile buffer, may be dissolved in the medium used for the cell culture or may be directly dissolved in the cell culture.

In a second embodiment of the invention, the receptacle containing the oxygen-carrying molecules may be part of a bioreactor.

Figure 2:
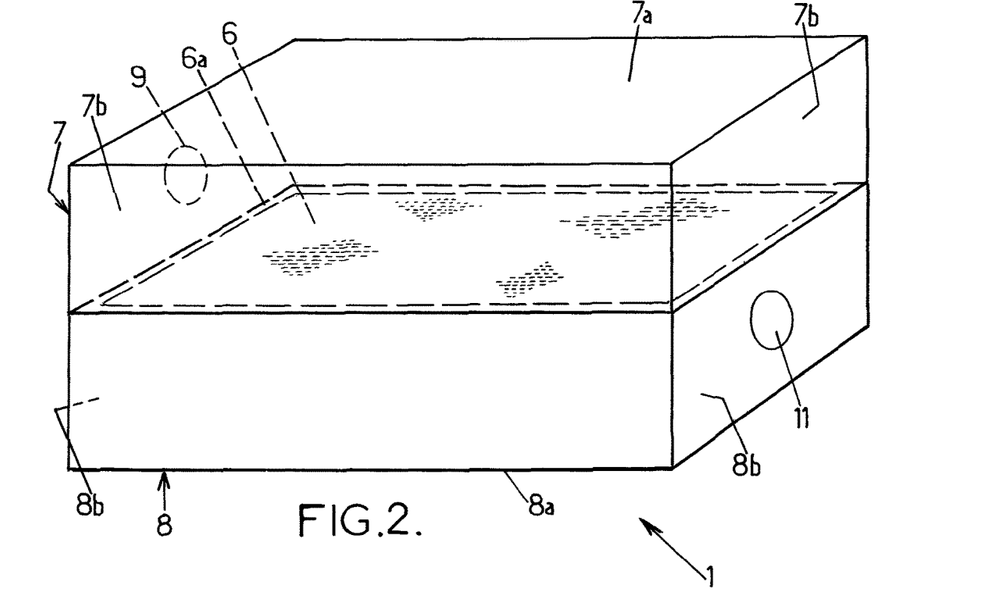
FIG. 2 is perspective view of a double-chamber bioreactor according to a second embodiment of the invention.

FIG. 2 illustrates a bioreactor 1 according to a second embodiment of the present invention, in which the bioreactor 1 comprises:
- an upper culture chamber 7 presenting an upper wall 7a and four lateral walls 7b forming a hollow, open-ended rectangular-shaped housing;
- a lower oxygen chamber 8 presenting a lower wall 8a and four lateral walls 8b forming a hollow, open-ended rectangular-shaped housing, and
- a dividing structure 6a arranged between and linking the upper culture chamber 7 and the lower oxygen chamber 8, said dividing structure comprising a oxygen-permeable membrane 6.

The bioreactor 1 may be fabricated from gas-impermeable materials, in particular oxygen-impermeable materials. The upper culture chamber 7 and lower oxygen chamber 8 are thus substantially air-tight to the exterior, except for oxygen diffusion through the oxygen-permeable membrane 6.

In certain embodiments of the invention, the bioreactor 1 is fabricated at least in part from a polymeric material such as polystyrene, poly(carbonate), polypropylene, or copolymers of aromatics and polyolefins, which can be processed using standard methods such as free-form molding, micromolding, injection molding (e.g., reaction or thermoplastic injection molding, punching, etc.), hot embossing, CNC machining, laser direct write, microelectrodischarge machining, etc. Thermal bonding of thermoplastic materials is another useful technique that may be used.

The bottom of the bioreactor, which can be the lower wall 8a of the lower oxygen chamber 8, is preferably formed from a rigid substrate sufficiently strong to support and stabilize the remaining portion of the structure 1. Examples of rigid substrate include, but are not limited to, silicon, glass, plastics such as polycarbonate, and plexiglass.

In one particular variant, at least one wall, preferably the upper wall 7a, of the bioreactor comprises a substantially transparent material permitting optical observation by a user.

In certain preferred variants of the present embodiments, biocompatible materials (i.e., materials that will not significantly inhibit or adversely affect cell viability and proliferation and/or adversely affect other biological components such as metabolites produced by the cells) may be employed for those portions of the bioreactor that are in contact with cells or are used to deliver cells or other materials to the vessel, such as the upper chamber 7. Suitable materials include silicon, silicon dioxide (e.g., glass), ceramics, plastics such as poly(carbonate)s, acrylates, polypropylenes, polyethylenes, polyolefins, etc. In addition, nonbiocompatible materials (e.g., certain metals) can be employed provided they are coated with a biocompatible material.

The dividing structure 6a is fixed between the four lateral walls 7b of the upper culture chamber 7 and to the four lateral walls 8b of the lower oxygen chamber 8. The dividing structure 6a is disposed substantially horizontally and thus separates the otherwise-sealed upper culture chamber 7 and lower oxygen chamber 8.

The dividing structure 6a comprises an opening 6b closed by an oxygen-permeable membrane 6.

The oxygen-permeable membrane 6 is a membrane through which oxygen is able to diffuse. The oxygen-permeable membrane 6 can be incorporated as a structural component of the chamber, for example as part of the dividing structure 6a, or directly sealed to a lateral chamber wall 7b, 8b.

The opening 6b may be smaller than the horizontal surface of the dividing structure 6a. Alternatively, the opening 6b may span the entire surface between the respective lateral walls 7b, 8b, in which case the dividing structure 6a may be dispensed with and the oxygen-permeable membrane 6 may be directly attached to the lateral walls 5 (as shown on FIGS. 3 to 8). The membrane 6 may be attached using any technique known to the skilled person, and may for example be attached to the lateral walls 5 of the housing by fixing means, for example adhesion, crimping, thermosealing, etc.

Examples of oxygen-permeable membrane include, but are not limited to, fluoropolymer, polytetrafluoroethylene (TEFLON®), silicone or polydimethylsiloxane (PDMS).

In general, said oxygen-permeable membrane may provide a 0.2 μm vent barrier.

In certain embodiment of the invention, the permeability (i.e. product of diffusivity or solubility) of the membrane 6 to oxygen is approximately equal to that of PDMS, i.e. 800 barrer (1 Barrer=$10^{-11}$ $(cm^3\ O_2)$ cm $cm^{-2}$ $s^{-1}$ $mmHg^{-1}$). In certain other embodiments of the invention the permeability of the membrane to oxygen is greater than 800 Barrer. In certain other embodiments of the invention the permeability of the membrane to oxygen is either between approximately 600 and 800 Barrer, between approximately 400 and 600

Barrer, between approximately 200 and 400 Barrer, or between approximately 80 and 200 Barrer.

The oxygen-permeable membrane 6 may also be transparent.

The oxygen-permeable membrane 6 positioned in the bioreactor may have any suitable size or geometric shape but one must be selected so that there is sufficient oxygen diffusion to supply the amount needed for cell metabolism. Those skilled in the art will be able to adapt these features, and the material of which the membrane is made, to the customary bio-technological requirements.

PDMS represents an attractive choice for the oxygen-permeable membrane 6 fabrication for a number of reasons. PDMS is highly permeable to gas, which allows sufficient oxygen to diffuse into the medium while simultaneously allowing carbon dioxide and other gases to escape. PDMS is highly hydrophobic, which minimizes water loss to evaporation. It is biocompatible, can withstand autoclaving temperatures, and is transparent to visible light. Poly(methyl methacrylate) (PMMA) represents another attractive material for fabricating the oxygen-permeable membrane 6. This material offers greater mechanical stability while also providing excellent optical transparency in the visible region, which is important for systems that include an optical sensor. In general, other materials that provide a high degree of optical transparency can also be used. Typically such materials will transmit electromagnetic radiation without substantial scattering and/or absorption over thicknesses of interest herein. For example, preferred materials may attenuate incident electromagnetic radiation by 50% or less, 75% or less, 85% or less, 90% or less, 95% or less, or 99% or less, over a path length of 1 cm, 1 mm, 0.5 mm, 1 mm, etc. The transparency of a material can vary in a wavelength-dependent manner. Preferred materials have a high degree of transparency over wavelengths ranging between approximately 400 and 1100 nm, preferably between approximately 400 and 800 nm.

The bioreactor 1 may of course be scaled to any size according to the design needs of the bioreactor.

Examples of conventional sizes for bioreactors are 190× 95×62 mm (L×W×H), 275×120×80 mm and 275×120×80 mm.

In one particular variant, the bioreactor 1 has a smaller size such as 100-125 by 45-60 by 8-15 mm.

In another variant, the bioreactor 1 may be a so-called microbioreactor, i.e. a device wherein the upper culture chamber has an interior volume of less than 1 ml. In other variants, the upper culture chamber may have an interior volume less than 200 µl. In yet another variant, the upper culture chamber may have an interior volume between 50 µl and 100 µl inclusive. In yet another variant, the upper culture chamber may have an interior volume between 5 µl and 50 µl inclusive. In yet another variant, the upper culture chamber may have an interior volume between 5 µl and 10 µl inclusive.

Small interior volumes of upper culture chamber 7 offer a number of advantages as they imply smaller diffusion times, which aids in exchange of gases. In these variants where the bioreactor 1 is a microbioreactor, the lower oxygen chamber has an interior volume equal or superior to the upper culture chamber volume.

The present embodiment offers the following features and advantages, among others: (1) water losses from evaporation may be replaced by osmosis from the lower chamber 8; (2) oxygenation is provided by the oxygen-carrying molecules which allow a better diffusion through the membrane 6; (3) contact with large reservoir of pH-neutral solution allows neutral pH to be maintained in the cell compartment (i.e. the upper culture chamber 7); (4) the process remains batch if only gases and water permeate membrane 6, while if the membrane 6 allows nutrients, products, etc., to also permeate, process becomes semi-batch or continuous; (5) the design allows control of the oxygen gradient within the culture chamber 7 by controlling oxygen content of the lower oxygen chamber 6, and atmosphere of the upper culture chamber 7.

As illustrated in FIG. 2, the bioreactor 1 may preferentially further present at least one opening 9 disposed in the upper culture chamber 7, for example in the upper wall 7a or in one or more of the laterals walls 7b. As illustrated in FIG. 2, the opening 9 is disposed in the lateral wall 7b in proximity to the membrane 6.

The opening 9 may be extended by a tube 10 which may be provided with a cap 11 to close-off the upper culture chamber 7 (FIG. 3) when needed.

The opening 9 is arranged to be adapted to connect to a filling device (not illustrated), for example a pipette or a continuous-feed type of device, for receiving fluid such as culture medium destined for the upper culture chamber 7. Similarly, a second opening 9 similar to the first, not illustrated, may be provided to the upper culture chamber 7 for removing fluid at the same time as being able to introduce fluids.

Furthermore, as also illustrated in FIG. 2, an opening 11 may also be disposed in the lower oxygen chamber 8, for example in the lower wall 8a or in one of the lateral walls 8b in proximity to the membrane 6. The opening 11 is preferably provided with an oxygen-permeable membrane, of similar construction to the oxygen-carrying membrane 6, to reduce ingress of foreign matter.

The opening 11 may be extended by a tube 12 in communication with an oxygen source, for example ambient air, pure oxygen, etc. The free extremity of the tube 12 may further be provided with a valve device 13 adapted to be closed or regulated to limit oxygen transfer.

Figure 3:
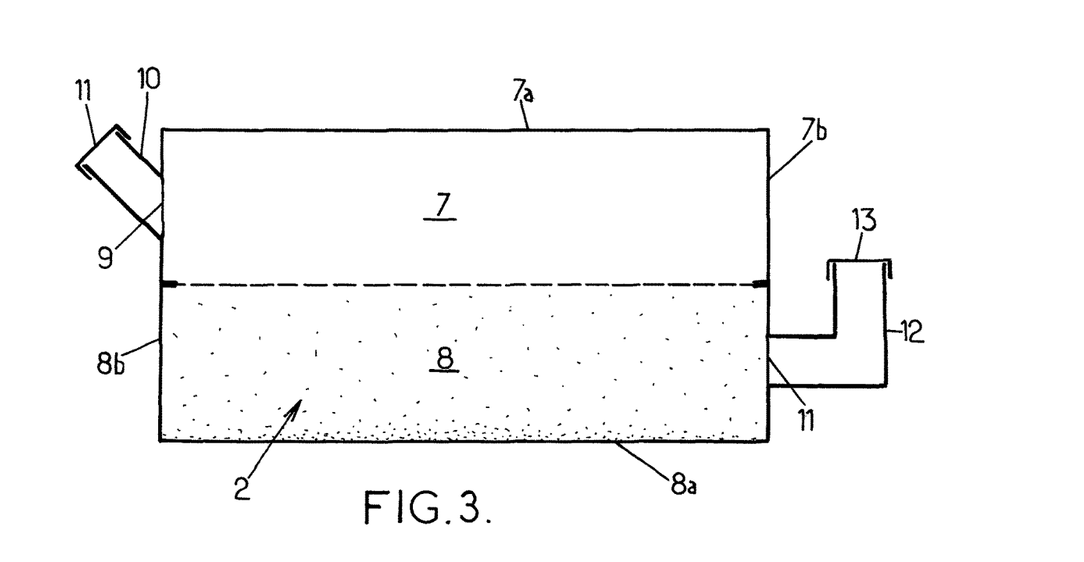
FIG. 3 is the bioreactor of FIG. 2 in a side elevation view according to a variant of the second embodiment.

As illustrated in FIG. 3, the lower chamber 8 is filled with oxygen-carrying molecules 2 for operation.

According to the invention, the oxygen-carrying molecules 2 are isolated or engineered biological molecules that are capable to transport oxygen. Said oxygen-carrying molecules are selected from the group consisting of: hemoglobin-based oxygen carriers, perfluorocarbons and extracellular haemoglobins isolated from annelids.

Haemoglobin-based oxygen carriers (HBOCs) and perfluorocarbons (PFCs) are two viable categories of oxygen therapeutics that currently exist. Haemoglobin taken directly from red blood cells can not be used as an oxygen carrier. To avoid spontaneous breakdown of haemoglobin and the toxicity of haemoglobin extracted from red blood cells, haemoglobin-based oxygen carriers use purified human haemoglobin (Riess et al. Chem Rev 2001, 101:2797), animal (bovine) haemoglobin (Lok et al Nature 2001, 410:855) or recombinant haemoglobin (Looker et al Nature 1992, 356: 258) as raw materials. Each chain of purified haemoglobin is then covalently bridged with other globin chains or microencapsulated. Perfluorocarbons are liquid fluorinated hydrocarbon compounds capable of dissolve large amount of oxygen and then deliver this oxygen.

Examples of HBOCs include, but are not limited to, cross-linked haemoglobins such as Oxyfluor® from Hemagen, HemAssist® from Baxter; polymerized haemoglobins such as PolyHeme® from Northfield laboratories, Hemopure® from Biopure; or conjugated haemoglobins such as PHP® from Apex Bioscience, Hemospan® from Sangart.

Examples of PFCs include, but are not limited to, Oxygent® from Alliance or Oxycyte® from Synthetic blood.

In another embodiment, the extracellular heamoglobins isolated from marine annelids are isolated from worms belonging to Arenicolidae family or Nereididae family.

Preferably, said haemoglobin are isolated from *Arenicola marina* or from *Nereis virens*, also called *Nereis diversicola*, *Neanthes virens* or *Hediste diversicolor*.

The oxygen-carrying molecules 2 may be in aqueous solution. As such, the bioreactor 1 may be directly provided with the lower oxygen chamber 8 containing an aqueous solution comprising the oxygen-carrying molecules 2.

When the oxygen-carrying molecules are selected in the group of HBOCs and haemoglobin isolated from marine annelids, said oxygen-carrying molecules may be in a lyophilized form.

When the oxygen-carrying molecules are in a lyophilized form, the oxygen-carrying molecules must be dissolved in a buffer. Said buffer may be introduced in the lower oxygen chamber 8 through the opening 11. In this case, the opening 11 connected to the tube 12 and the cap 13 are adapted for any suitable device, such as a pipet, that allows the filling of the lower oxygen chamber 8 with the buffer.

Alternatively, the bioreactor may be provided in a kit with a container containing the oxygen-carrying molecules in a lyophilized or thawed form. The oxygen-carrying molecules in a lyophilized or thawed form must be dissolved before use in an aqueous solution. The lower oxygen chamber 8 of the bioreactor is then filled before use with the aqueous solution comprising the oxygen-carrying molecules.

Alternatively, the bioreactor 1 may be provided in a kit with a container containing an aqueous solution comprising the oxygen-carrying molecules 2. The lower oxygen chamber 8 of the bioreactor is then filled before use with the aqueous solution comprising the oxygen-carrying molecules.

It is to be noted that the bioreactor 1 according to the present embodiment may be provided with a supply of oxygen-carrying molecules 2 already loaded in oxygen in the lower oxygen chamber 8, in which case it is not necessary to provide an oxygen source, for example oxygen inlet 11. Such a bioreactor, however, only has a limited life. Such a bioreactor may be useful where a precise amount of oxygen needs to be diffused across the oxygen-permeable membrane 6, or in application needing a disposable bioreactor 1.

Alternatively, on may provide a bioreactor 1, in which oxygen-carrying molecules 2 in the lower oxygen chamber 8 are empty of oxygen. In such a case, the oxygen inlet 11 may charge the molecules 6 with oxygen.

Furthermore, it is envisaged that the lower oxygen chamber 8 forms a detachable part of the bioreactor 1 which can be exchanged with off-the-shelf oxygen chambers 8 preloaded in oxygen, with or without an oxygen inlet 11.

In operation, the upper culture chamber 7 is filled through the opening 9 with cells in culture medium. The lower oxygen chamber 8 is filled with an aqueous solution comprising oxygen-carrying molecules as described above. The oxygen-carrying molecules are adjacent, or preferably in direct physical contact with, the oxygen-permeable membrane 6. The oxygen-carrying molecules function in a simple gradient of partial pressure of oxygen. Thus, when $pO_2$ of the upper culture chamber 7 is inferior to the $p_{50}$ of the oxygen-carrying molecules, oxygen is released from the molecules and when the $pO_2$ of the upper culture chamber 7 is superior to the $p_{50}$ of the oxygen-carrying molecules, oxygen is uploaded on the molecule without the necessity of any cofactor. Hence a gradient is created between both chambers of the bioreactor as the upper culture chamber 7 comprising the cells consumes oxygen in function of cell growth.

As shown in FIG. 10, oxygen diffusion across a oxygen-permeable membrane is considerably increased when oxygen-carrying molecules are used compared to simple oxygen diffusion.

Figure 4:
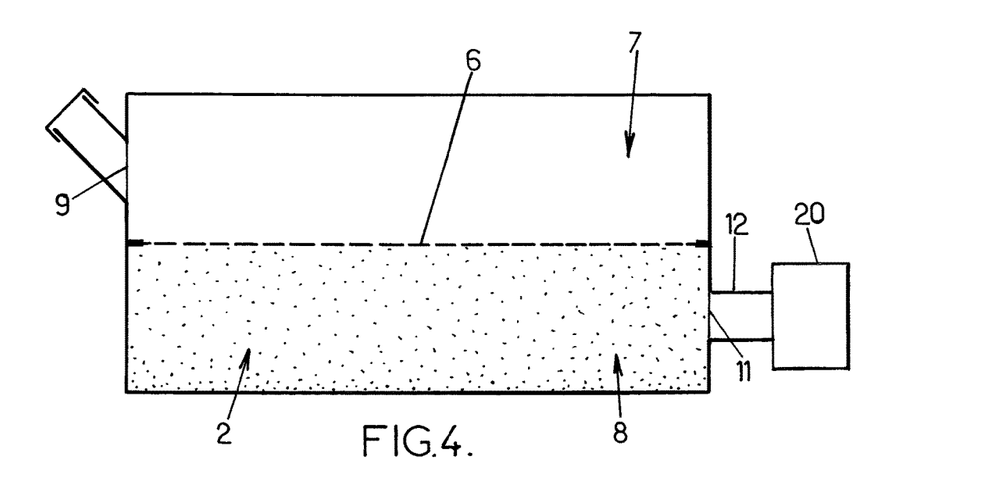
FIG. 4 is the bioreactor of FIG. 3 in a side elevation view according to a variant of the second embodiment.

In a third embodiment, illustrated at FIG. 4, the bioreactor as described above for the second embodiment, further comprises an oxygen injection device 20 attached to the oxygen opening 11 via a tube 12.

The oxygen injection device 20 may for example be an oxygen pump adapted to inject oxygen through the opening 11.

The oxygen injection device 20 may absorb oxygen from the atmosphere, purifying if necessary, or may contain an internal oxygen reservoir as a source to inject oxygen into the lower oxygen chamber 8 filled with oxygen-carrying molecules 2.

Depending on the volume flow rate of the oxygen injection device 20, the oxygen injection into the lower oxygen chamber 8 creates a micro-circulation, for example eddies, of the oxygen-carrying molecules 2 which allows a more homogeneous oxygen charge of the oxygen-carrying molecules 6, and thus a more effective oxygenation of the upper culture chamber 7 through the membrane 6.

The oxygen injection device 20 may further comprise a pressure relief valve to allow reduction of $pO_2$ in the lower oxygen chamber 8.

Figure 5:
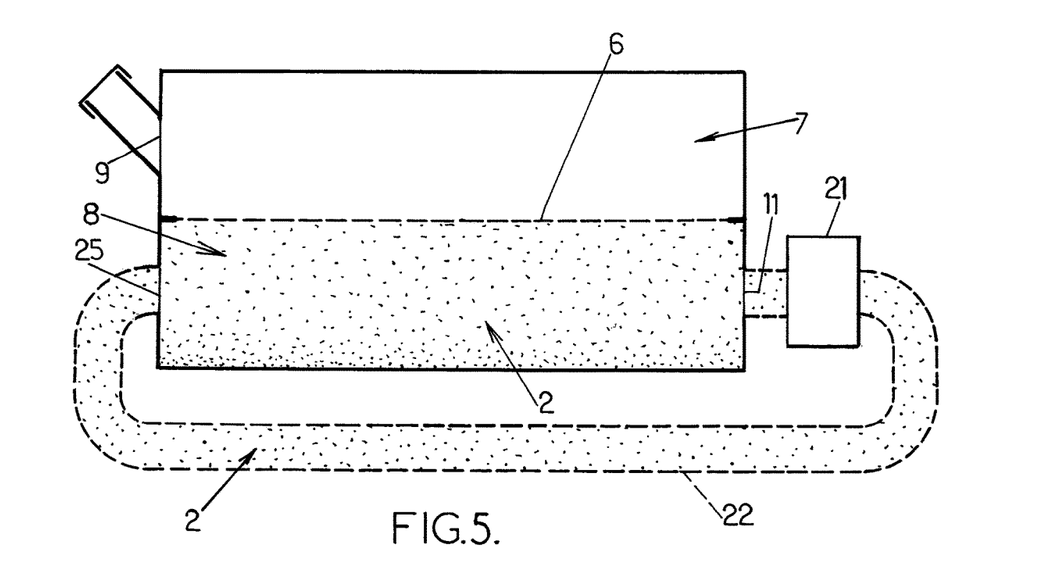
FIG. 5 is the bioreactor of FIG. 4 in a side elevation view according to a variant of the second embodiment.

In a variant of this third embodiment, as illustrated in FIG. 5, the lower oxygen chamber 8 comprises a second opening 25. The second opening 25 is preferably positioned at the distal end of the lower chamber 8 with respect to the opening 11.

In this variant, a circulation device 21 replaces the oxygen injection device 20. The circulation device 21 is connected to both the opening 11 and the opening 25 via oxygen-permeable tube 22 and is adapted to circulate the oxygen-carrying molecules 2 through the tube 22. The tube 22 is positioned in an oxygen source, such as ambient air, or an oxygen-rich environment.

As used herein, the term "tube" refers to a hole of constant or systematically varied cross-sectional area through a material. Generally a tube has a defined cross-sectional geometry, which may be rectangular, ovoid, circular, or one of these geometries with an imposed finer feature, such as indentations, etc. A "microfluidic tube", also referred to herein as a "microtube", has at least one dimension of less than 1000 microns. Typically the characteristic dimensions of a cross-section of a microtube (e.g., height and width of a tube with a rectangular cross-section, diameter of a microtube with a circular cross-section, etc.) will both be less than 1000 microns. It will be understood that the cross-section is to be taken perpendicular to the length of the microtube and that the length of the microtube is often greater than 1000 microns. It will further be appreciated that any of the tubes in the devices described herein may be, and typically is, a microfluidic tube.

One example of microtube, suitable for a bioreactor having the following size: 100-125×45-60×8-15 mm, is a microtube of about 200 μm width×100 μm height.

The permeable tubes 22 may be made from the same material as the oxygen-permeable membrane 6.

The circulation device 21 may for example be a fluid pump, for example a peristaltic pump or a flat valve pump. As used herein, the term "pump" refers to any means that allow the oxygen-carrying molecules to circulate in the tube structure.

The circulation device 21 forces a circulation of the oxygen-carrying molecules 2 into the opening 11 via a portion of oxygen-permeable tube, through the lower oxygen chamber 8 filled with oxygen-carrying molecules 2, out of the second opening 25, and back to the circulation device 21 via the oxygen-permeable tube 22. The circulation device 21 thus circulates the oxygen-carrying molecules through the lower chamber 8.

The oxygen-carrying molecules 2 load oxygen when circulating through the oxygen-permeable tube 22 and discharge oxygen from the lower oxygen chamber 8 to the upper culture chamber 7 via the oxygen-permeable membrane 6, according to partial pressures as explained above.

The person skilled in the art will be able to determine the flow rate and flow velocity of the circulation device 21 according to the parameters of the bioreactor (in particular according to its size), in particular in function of the oxygen requirement of the cell culture and the porosity of the oxygen-permeable tube 22 through which oxygen is charged.

Furthermore, according to another variant of this embodiment, the circulation device 21 may be adapted to reverse its flow direction in order to alternate the direction of circulation of the oxygen-carrying molecules in the lower chamber 8.

The alternated flow of circulation allows a better homogenization and distribution of the oxygen-carrying molecules, and thus a better transfer of oxygen to the upper culture chamber 7.

According to another variant of this embodiment, the circulation device 21 comprises two pumps in tandem: a first pushing the fluid circulation and the second one drawing the fluid circulation. The two pumps may reverse their circulation direction so as to draw the fluid in the reverse direction. The two pumps may for example be placed adjacent each of the openings 11, 25.

Of course, the person skilled in the art will be able to adapt the functioning of the circulation device 21 according to his design objectives.

Figure 6A:
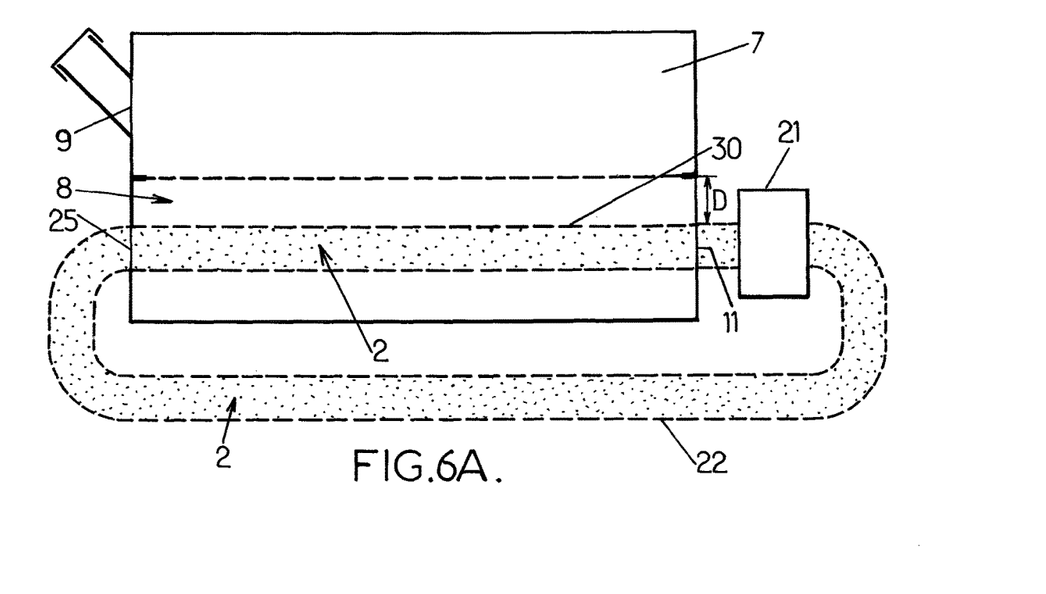
FIG. 6a is the bioreactor of FIG. 5 in a side elevation view according to a variant of the second embodiment.

According to yet another variant illustrated at FIG. 6A, the bioreactor 1 of FIG. 5, may further comprise a oxygen-permeable tube 30 connecting the opening 9 and the second opening 25 and disposed within the lower chamber 8.

In this variant, the lower chamber 8 is empty of oxygen-carrying molecules. Instead, the oxygen-carrying molecules 2 are contained within the closed-circuit comprising:
the circulation device 21,
the oxygen-permeable tube 22, and
the oxygen-permeable tube 30.

The oxygen-permeable tube 30 is disposed adjacent to the oxygen-permeable membrane 6, for example at a small distance D from said membrane chosen according to Fick's law of diffusion. Preferably the oxygen-permeable tubes 30 are in direct contact with the membrane 6.

Figure 6B:
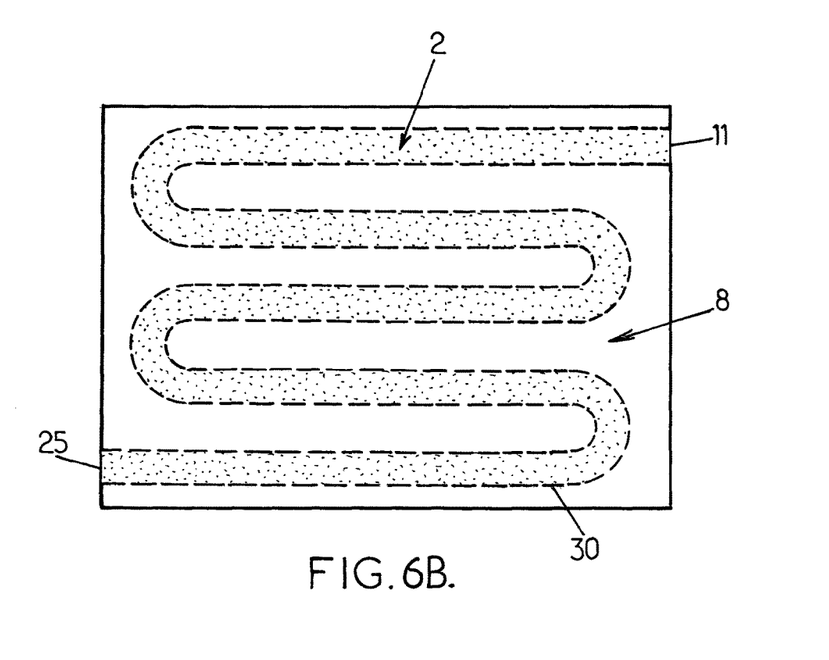
FIG. 6b is an exemplary plan view of oxygen-permeable tube of FIG. 6a, FIG. 7 is a perspective view of a double-chamber bioreactor according to a third embodiment of the invention.

The oxygen-permeable tube 30 may form channels, and may be straight, winding, circulating, etc. between the opening 9 and the opening 25. For example, as illustrated at FIG. 6B illustrating a plan view of the oxygen-permeable tube 30, the tube 30 has a winding configuration through the lower oxygen chamber 8.

The winding configuration along all or part of the length of the tube 30 with multiple turns and bends results in a tube with considerably greater actual length than the distance of a single straight line extending between the openings 11, 25. Having a longer effective length results in a lower effective flow rate per unit of oxygen diffusion than would otherwise be the case when a constant pressure source is used to drive the flow and thus avoiding the need to set the pressure at extremely low values. The oxygen-permeable tube 30 may for example have between 100 and 300 turns, or even more depending on space constraints, i.e. the total length of the tube 30 is approximately 100 to 300 times or more greater than the length of the lower oxygen chamber 8 between the openings 11, 25.

Figure 7:
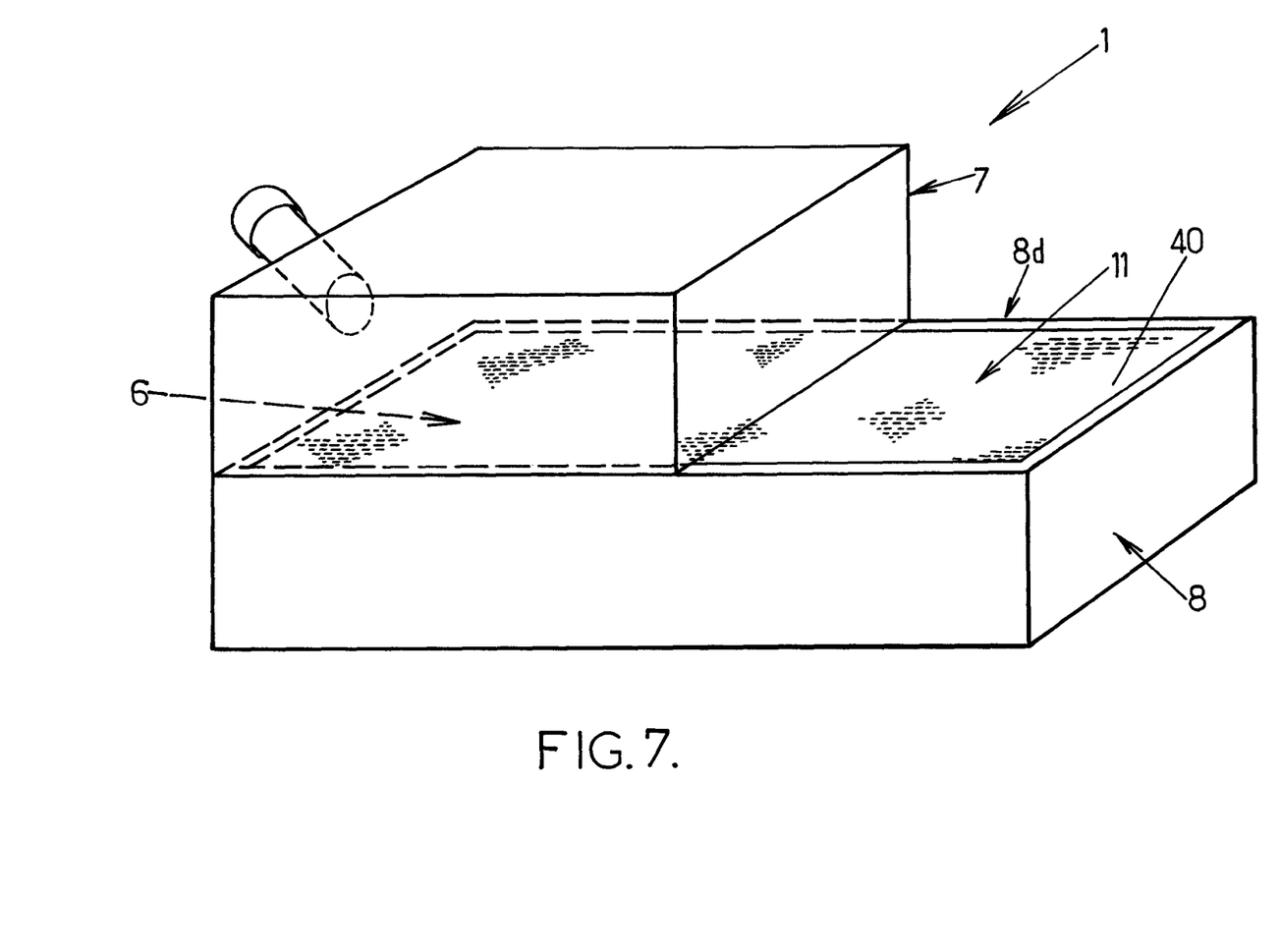

According to a fourth embodiment, as illustrated at FIG. 7, the bioreactor 1 according to any one of the one to three preceding embodiments as illustrated at FIGS. 2 to 6 is characterized by an opening 11 spanning a substantial part of the surface of the lower oxygen chamber 8.

According to this a variant of this embodiment, the lower oxygen chamber 8 is larger than the culture chamber 7 and comprises an overhanging portion 8d on one or more lateral sides along a direction for example parallel to the oxygen-permeable membrane 6 onto which the cell culture is placed.

The overhanging portion 8d comprises the oxygen opening 11 comprising a second oxygen-permeable membrane 40 in sealing contact with, and covering the entire opening 11.

The opening 11 may span a relatively large area of the upper side of the overhanging portion 8d, for example the whole upper side of the overhanging portion 8d, and may be covered by the membrane 40.

Figure 8:
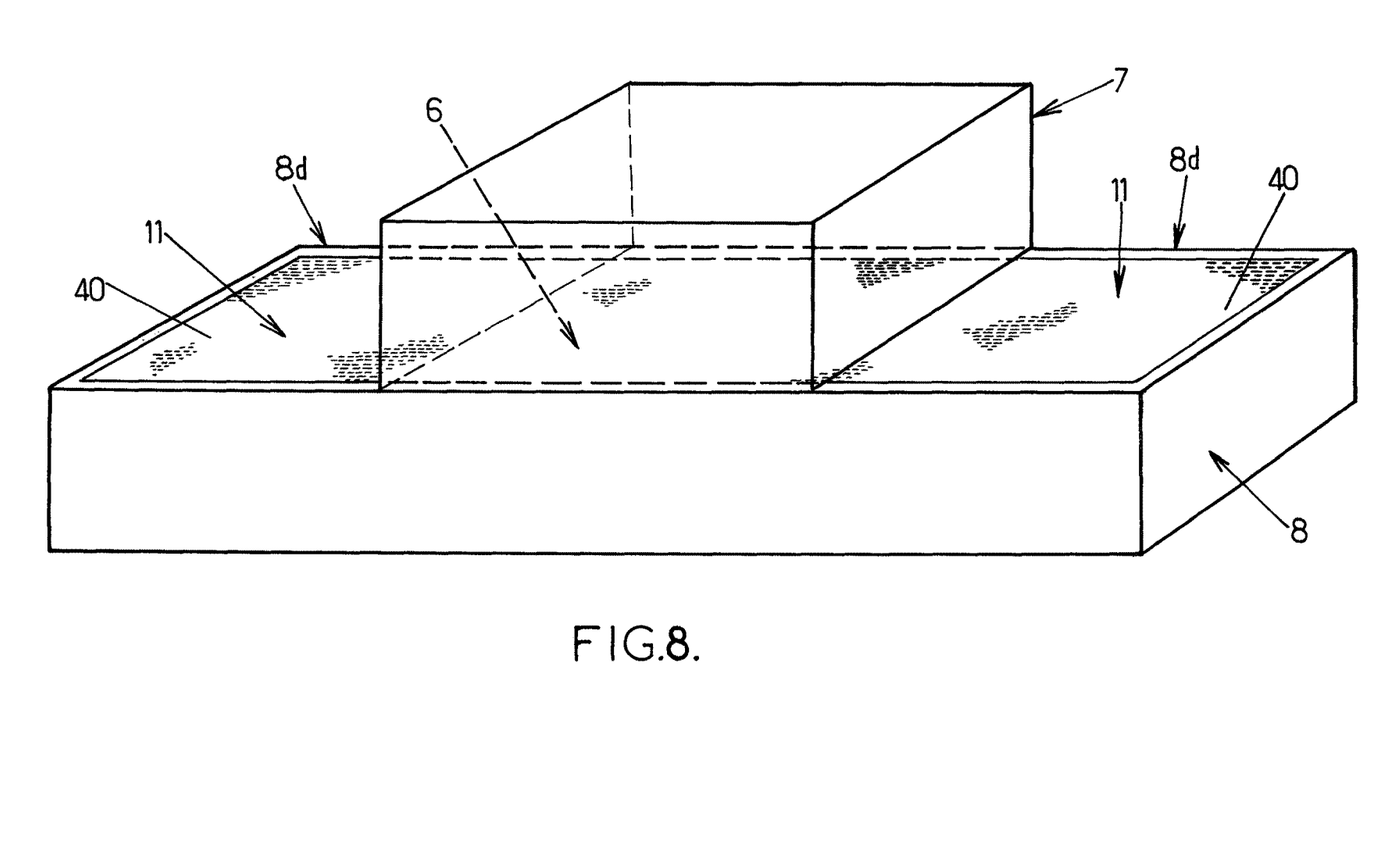
FIG. 8 is a perspective view of a double-chamber bioreactor according to a variant of third embodiment of the invention illustrated at FIG. 7, FIG. 9a-b are two plan views cross-section of the lower oxygen chamber according to variants of a fourth embodiment.

However, it is entirely within the reach of the skilled person to conceive a bioreactor 1 in which the lower oxygen chamber 8 presents two or more overhanging portions 8d over two or more of the lateral sides of the upper culture chamber 7 (FIG. 8). Furthermore, such a bioreactor may present one or more openings 11 covered by a membrane 40 positioned on upper, lateral, or lower surfaces of the oxygen chamber 8. This allows the oxygen-carrying molecules to load fresh oxygen from both side of the lower culture chamber 8; therefore the uniformity of oxygen concentration distribution to the upper oxygen chamber is better.

In this embodiment, the oxygen-carrying molecules 2 load oxygen through the membrane 40 and then diffuse it to upper culture chamber 7 via the oxygen-permeable membrane 6.

Figure 9A:
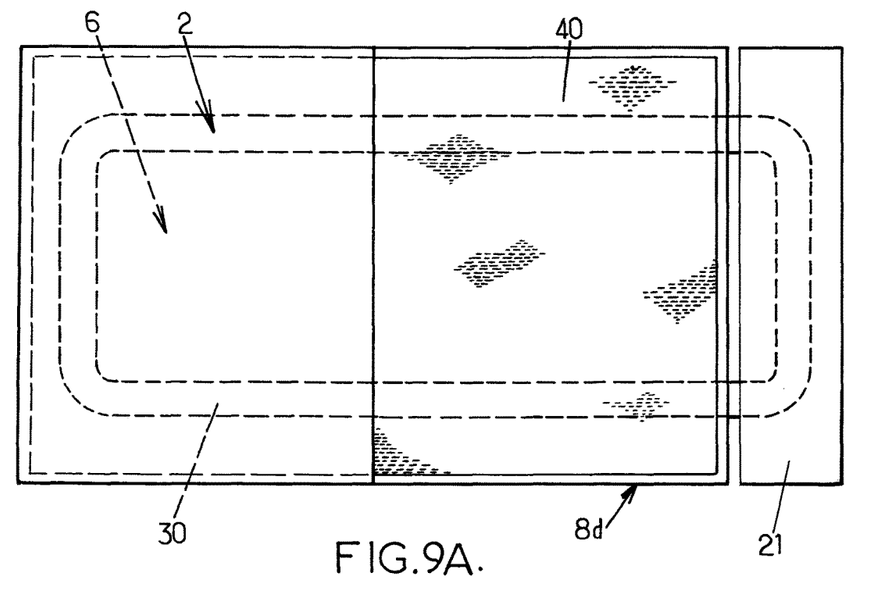
Figure 9B:
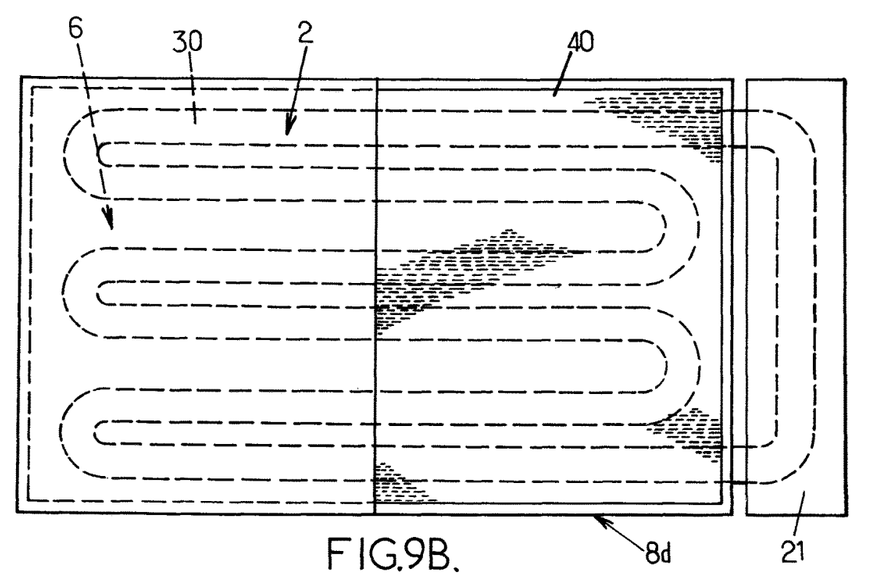

In a variant illustrated in FIGS. 9A and 9B, the bioreactor 1 of the fourth embodiment as illustrated at FIGS. 7 and 8 further comprises a circulation device 21 similar to that of FIG. 5, 6A or 6B, connected to a oxygen-permeable tube 30 adapted to circulate the oxygen-carrying molecules 2 within the lower oxygen chamber 8.

The circulation device 21 is preferably disposed outside the lower oxygen chamber 8, and the oxygen-permeable tube 30 is disposed inside the lower oxygen chamber 8.

The circulation device 21 forces a circulation of the oxygen-carrying molecules through the oxygen-permeable tube 30 and back through the circulation device 21.

The circulation device 21 thus circulates the oxygen-carrying molecules 2 through the lower oxygen chamber 8, during which the oxygen-carrying molecules absorb ambient oxygen through the one or more membranes 40. More precisely, ambient oxygen from the atmosphere or an oxygen-rich volume diffuses across the membrane 40 into the lower oxygen chamber 8, from where it is absorbed by the oxygen-carrying molecules 2 via the oxygen-permeable tube 30, from where it is transferred by the circulation device 21 to a position adjacent the oxygen-permeable membrane 6, at which point the oxygen will diffuse from the oxygen-carrying molecule 2 to the cell culture via the oxygen-permeable membrane 6 by the process of partial oxygen pressure differential.

Of course, the skilled person will appreciate that positioning the oxygen-permeable tube 30 adjacent the membrane 40 according to Fick's law of diffusion, preferably in direct contact, will increase the oxygen diffusion between the oxygen source at the membrane 40 and the oxygen-carrying molecules 2 through the tube 30.

Furthermore, according to another variant of this embodiment, the circulation device 21 may be adapted to reverse its flow direction in order to alternate the direction of circulation of the oxygen-carrying molecules in the lower chamber 8.

The oxygen-permeable tube 30 may form any type of tube, and may be straight, winding, circulating, etc. inside the oxygen chamber 8. A winding tube 30 increases the net in-flow through greater surface area in contact with an oxygen source.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims.

In particular, the bioreactor as described above may comprise at least one inflow port connected to the upper culture chamber 7 to allow fresh culture medium to be continuously supplied to the upper culture chamber 7 and at least one outflow port connected to the upper culture chamber 7 to allow culture medium to be continuously removed from the upper culture chamber 7.

Medium leaving the upper culture chamber 7 through the outflow port flows to a collection chamber. The collection chamber can be of any convenient volume, typically at least 10% of the volume of the upper culture chamber.

A variety of methods can be used to control medium inflow and outflow rates. Gravity-driven flow can be achieved by elevating a medium reservoir above the height of the chemostat and maintaining the effluent reservoir below the level of the medium reservoir. By adjusting the relative heights of the medium reservoir, chemostat, and effluent reservoir, the total rate of medium inflow to and outflow from the first chamber can be controlled over a wide range. Since the culture vessel maintains a constant average volume, these rates will generally be equal except for insignificant contributions from evaporation.

Medium inflow and outflow can also be controlled using any of a variety of active means. Positive pressure can be exerted on the medium reservoir to cause medium to flow through the medium inflow port into the culture chamber 7. Alternately, negative pressure can be exerted on the effluent or medium outflow port. Pressure can be delivered using a constant pressure source or a motor-driven pump. Valves can be used to regulate the flow. Combinations of any of the foregoing methods can also be used.

Furthermore, the upper culture chamber 7 may be divided into: one medium compartment and one cell compartment, separated by a 10 kDa semi-permeable membrane. The 10 kDa semi-permeable membrane allows a continuous diffusion of nutrients into the cell compartment with a concurrent removal of any inhibitory waste product. An example of 10 kDa semi-permeable membrane is a cellulose acetate membrane such a polypropylene liner or a polytetrafluoroethylene liner. According to this embodiment, the opening 9 allows the filling of medium in the medium compartment, while the bioreactor must have a further opening in the upper culture chamber 7 that allows the filling of cells in the cell compartment.

According to the invention, the bioreactor as described in the various embodiment of the invention can be used for cell culture with suspension cells or adherent cells. Examples of cells that can be cultivated in the bioreactor of the invention include, but are not limited to, hybridomas, CHO cells, NSO cells, SF cells.

In another embodiment of the invention, the bioreactor can be specifically adapted to allow growth of anchorage-dependent cells such as HEK cells, BHK cells, or CHO cells. According to this embodiment, the upper culture chamber 7 comprises a surface that allows cell attachment. An example of such a surface includes, but is not limited to, a woven polyethylene terephtalate (PET) matrix.

Furthermore, in one embodiment of the invention, the bioreactor as described in the various embodiment of the invention can be operated in batch mode.

In another embodiment of the invention, the bioreactor as described in the various embodiment of the invention can be operated in fed-batch mode.

In another embodiment of the invention, the bioreactor as described in the various embodiment of the invention can be operated as a microchemostat. This bioreactor allows for continuous medium inflow and outflow and allow for precise control over growth conditions within the culture chamber. As is known in the art, a chemostat is a continuous culture system in which the supply of nutrients is determined externally and cell growth and/or biomass increase is limited by the availability of a selected nutrient. Either prokaryotic (bacteria) or eukaryotic (e.g., fungal, insect, mammalian, etc.) cells can be cultured in a chemostat. The growth-limiting nutrient can vary and is often a carbon source such as glucose, but can also be other nutrients, such as nitrogen source, specific amino acids, nucleotide precursors, trace minerals, etc. For purposes of the present invention, growth can also be limited by factors other than nutrient availability. pH or temperature can also be growth-limiting. In general, any factor that affects cell growth and can be externally controlled and maintained at a fixed level can be the growth-limiting factor in a chemostat. Generally nutrient availability is controlled by supplying a constant flow of medium of a given composition to a culture vessel and removing culture medium from the vessel at an equal rate (i.e., volume/time). Thus the bioreactor can comprise means for supplying a constant flow of medium to the culture vessel and means for removing culture medium from the vessel at an equal rate to the rate at which medium is supplied. Such means should be capable of operating while the bioreactor is being used to culture cells. Chemostat operation is often described in terms of the dilution rate D, which equals the flow rate F (volume/time) divided by the culture volume, V. The dilution rate, D, equals the specific growth rate, u, a measure of how fast a cell reproduces that reflects the intrinsic ability of the cells to reproduce under the given conditions. See Smith, H. L., et al, The Theory of the Chemostat: Dynamics of Microbial Competition (Cambridge Studies in Mathematical Biology), Cambridge University Press, Cambridge, England (1995) for additional details regarding chemostats and some of their uses.

"Constant growth conditions" or "chemostat conditions" refers to a situation in which environmental conditions that are physiologically relevant for cell growth are maintained at a fixed level (to within experimental error) so that on a statistical basis cells in the culture are exposed to an identical and constant environment over time. The biomass concentration and/or cell density thus remains constant within the culture vessel for a prolonged period of time, and the culture is in a steady state. It is noted that biomass concentration refers to weight of cells per unit volume (either dry or wet weight can be used), while cell density refers to the number of cells per unit volume. In many instances these parameters are directly related and can be used interchangeably, though exceptions exist such as situations in which cell division is inhibited, in which case cells can increase in volume but cannot divide. Another example is a population of cells that is synchronized with respect to cell cycle stage, in which case there can be an increase in total cell volume without an increase in cell number during G1, S, G2, and/or M phase and a sudden increase in cell number without a correspondingly large increase in total cell volume when cytokinesis takes place. The growth conditions can include concentration of dissolved gases (e.g., oxygen, carbon dioxide), the pH, the temperature, the biomass concentration, the cell density, the concentration of one or more nutrients, the concentration of one or more metabolic products, or any combination of the foregoing. By "prolonged period of time" is meant at least 5 times the turnover time (i.e., the time that would be required to completely fill an empty culture chamber), which is numerically equal to the reciprocal of the dilution rate. Preferably growth conditions and biomass concentration remain constant for at least 10 times the turnover time, more preferably at least 20 times the turnover time, yet more preferably at least 30 times, at least 50 times, at least 100 times the turnover time, or longer. It is important not only that the average concentrations of nutrients, oxygen concentration, etc., within the culture chamber remains constant but also that the contents of the chamber are well mixed, in order to avoid local differences in growth conditions.

The existence of constant growth conditions can be verified by assessing parameters such as pH, and biomass concentration (e.g., cell density) over time. Typically, the rate of change (dX/dt), of these 3 parameters (where X is pH, optical density) is less than 0.25, more preferably less than 0.1, and more preferably less than 0.05, and still more preferably less than 0.01 over a prolonged period of time to verify the existence of chemostat conditions. Appropriate corrections can be made for artefacts and/or measuring errors due, for example, to transient changes in the volume of medium in the culture chamber due to minor fluctuations in pressure driving medium inflow and outflow. Measuring the concentrations of various nutrients and/or metabolites (either online or offline) can also be used to verify the existence of constant physiological conditions.

While, a chemostat may be inoculated with only a single cell, in practice it is more typical to inoculate with a plurality of cells and to maintain chemostat conditions in a culture vessel with a plurality of cells. For example, a chemostat such as the microchemostats of the invention may be inoculated at a density of at least $10^2$ cells/ml, at least $10^3$ cells/ml, at least $10^4$ cells/ml, at least $10^5$ cells/ml, at least $10^6$ cells/ml, at least $10^7$ cells/ml, or more.

Preferably chemostat conditions are maintained for a prolonged period of time at cell densities of at least $10^2$ cells/ml, at least $10^3$ cells/ml, at least $10^4$ cells/ml, at least $10^5$ cells/ml, at least $10^6$ cells/ml, at least $10^7$ cells/ml, or more. In certain embodiments of the invention the chemostat is inoculated and/or maintained at a cell density of between $10^2$ and $10^8$ cells/ml, or within any range intermediate between these two values.

Another object of the invention is a kit comprising:
a bioreactor according to any of the embodiments and variants described here above, and
a container comprising oxygen carrying molecules.

As described here above, the oxygen-carrying molecules are isolated or engineered biological molecules that are capable to charge and discharge oxygen. Said oxygen-carrying molecules are selected from the group consisting of: hemoglobin-based oxygen carriers, perfluorocarbons and extracellular haemoglobins isolated from annelids, preferably from marine annelids.

Haemoglobin-based oxygen carriers (HBOCs) and perfluorocarbons (PFCs) are two viable categories of oxygen therapeutics that currently exist. Haemoglobin taken directly from red blood cells can not be used as an oxygen carrier. To avoid spontaneous breakdown of haemoglobin and the toxicity of haemoglobin extracted from red blood cells, haemoglobin-based oxygen carriers use purified human haemoglobin (Riess et al. Chem Rev 2001, 101:2797), animal (bovine) haemoglobin (Lok et al Nature 2001, 410:855) or recombinant haemoglobin (Looker et al Nature 1992, 356: 258) as raw materials. Each chain of purified haemoglobin is then covalently bridged with other globin chains or microencapsulated. Perfluorocarbons are liquid fluorinated hydrocarbon compounds capable of dissolve large amount of oxygen and then deliver this oxygen.

Examples of HBOCs include, but are not limited to, cross-linked haemoglobins such as Oxyfluor® from Hemagen, HemAssist® from Baxter; polymerized haemoglobins such as PolyHeme® from Northfield laboratories, Hemopure® from Biopure; or conjugated haemoglobins such as PHP® from Apex Bioscience, Hemospan® from Sangart.

Examples of PFCs include, but are not limited to, Oxygent® from Alliance or Oxycyte® from Synthetic blood.

In another embodiment, the extracellular haemoglobins isolated from marine annelids are isolated from worms belonging to Arenicolidae family or Nereididae family.

Preferably, said haemoglobin are isolated from *Arenicola marina* or from *Nereis virens*, also called *Nereis diversicola, Neanthes virens* or *Hediste diversicolor*.

According to a variant, the kit comprises a container comprising an aqueous solution comprising the oxygen-carrying molecules.

In another variant, when the oxygen-carrying molecules are selected in the group of HBOCs and haemoglobin isolated from marine annelids, said oxygen-carrying molecules may be in a lyophilized form. In another variant, when the oxygen-carrying molecules are haemoglobins isolated from marine annelids, said oxygen-carrying molecules may be thawed. In these last two variants of the kit, the kit may further comprises a second container containing a buffer suitable for dissolving the lyophilized or thawed oxygen-carrying molecules.

Examples

The following device was designated according to FIG. 8 and having a guide system as described in FIG. 9B:
  size of the bioreactor: about 115×60×15 mm (length× height×width), This size allows an easy and secure storage and minimum space requirements in any $CO_2$ incubator, oxygen-permeable membrane in polycarbonate: 25 µm
oxygen-permeable tube size: 200 µm (width)×100 µm (height),
length of oxygen-permeable tube: 20 m,
number of turns and bends of the tube: 200,
length of the upper culture chamber: 40 mm,
total liquid volume inside the tube: 4 ml,
two micro-pumps having their own embedded energy,
flow-rate of the pumps: 10/min (flow velocity: 50 mm/min),
operation mode: repetitions of 10 min forth flow and 10 min back flow,
total inflow: 0.2 ml/min,
dwelling time in oxygen releasing region: 0.8 min,
dwelling time in oxygen intake region: 1.2 min.

This type of bioreactor allows cell culture to reach a concentration higher than the one from conventional cell culture disposables which is usually comprised between $10^7$ and $10^8$ cells/ml. Consequently, the concentration of expressed proteins (recombinant protein of interest such as an antibody for example) is increased from 50 to 100 times compared to standard cultures.

Oxygen Diffusion Across an Oxygen Permeable Membrane Experiments

The bioreactor as described above was used.

An oxygen microelectrode WPI was calibrated according to manufacturer's instructions.

50 ml of $H_2O$ milli-Q were deoxygenated with nitrogen bulled during 20 minutes.

The culture chamber and the oxygen chamber of the bioreactor were filled with 2*10 ml of deoxygenated $H_2O$ and then closed.

PO2 was measured in t0 in the culture chamber using a microelectrode.

20 ml of a solution comprising 5 g/l of extracellular haemoglobin isolated from marine annelids were oxygenated with air bulling.

20 ml of $H_2O$ milli-Q were oxygenated with air bulling.

The oxygen chamber was filled with 20 ml of oxygenated $H_2O$ milli-Q or with 20 ml of oxygenated haemoglobin.

The pO2 of the culture chamber was then measured at different time points: 10, 20, 30 and 40 minutes.

Results are shown in FIG. 10: extracellular haemoglobin from marine annelids considerably increases oxygen diffusion across the oxygen-permeable membrane in comparison to simple oxygen diffusion.

The invention claimed is:

1. A bioreactor comprising:
at least one first chamber comprising cells in a culture medium and to provide growth conditions suitable for cell culturing; and
a receptacle comprising:
a second chamber for said bioreactor, at least partially defined by an oxygen-permeable membrane, and
a plurality of oxygen-carrying molecules contained within said second chamber, said oxygen carrying molecules being chosen from extracellular hemoglobins isolated from worms belonging to Arenicolidae family or Nereididae family, said oxygen-carrying molecules being in a form selected from the group consisting of dissolved in a sterile buffer suitable for cell culture, dissolved in a medium used for cell culture, dissolved in a cell culture, lyophilized, and thawed,
wherein said receptacle does not comprise any hollow fiber system, and
wherein said receptacle is positioned within said first chamber.

2. The bioreactor according to claim 1, wherein said oxygen carrying molecules are in a dissolved form in a buffer suitable for cell culture, a dissolved form in a medium used for cell culture, or a dissolved form in a cell culture.

3. The bioreactor according to claim 1, wherein said oxygen carrying molecules are in a lyophilized or thawed form.

4. The bioreactor according to claim 1, further comprising at least one inflow port connected to the first chamber to allow fresh culture medium to be continuously supplied to the first chamber and at least one outflow port connected to the first chamber to allow culture medium to be continuously removed from the first chamber.

5. The bioreactor according to claim 1, wherein said second chamber is entirely defined by an oxygen-permeable membrane.

6. The bioreactor according to claim 1, wherein said second chamber is partially defined by an oxygen-permeable membrane and further partially defined by at least one substantially rigid panel.

7. The bioreactor according to claim 6, wherein:
said at least one substantially rigid panel has an upper and lower surface and a cutout,
a first oxygen permeable membrane covers the cutout with respect to the upper surface of said at least one substantially rigid panel,
a second oxygen-permeable membrane covers the cutout with respect to the lower surface of said at least one substantially rigid panel, and
said oxygen-carrying molecules positioned between said first and second oxygen-permeable membranes.

* * * * *